(12) United States Patent
Schwarzkopf et al.

(10) Patent No.: US 9,683,258 B2
(45) Date of Patent: Jun. 20, 2017

(54) EFFICIENT SENSOR FOR DETECTING AND DETERMINING THE CONCENTRATIONS OF TARGETS

(75) Inventors: Kevin Robert Schwarzkopf, Camas, WA (US); Andrei L. Gindilis, Vancouver, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 1880 days.

(21) Appl. No.: 12/780,157

(22) Filed: May 14, 2010

(65) Prior Publication Data

US 2011/0280766 A1 Nov. 17, 2011

(51) Int. Cl.
*G01N 27/02* (2006.01)
*C12Q 1/68* (2006.01)
(Continued)

(52) U.S. Cl.
CPC ....... *C12Q 1/6816* (2013.01); *G01N 27/3276* (2013.01); *G01N 33/5438* (2013.01);
(Continued)

(58) Field of Classification Search
CPC ............. G01N 27/126; G01N 33/0031; G01N 27/3276; G01N 33/5438; G01N 33/54306
(Continued)

(56) References Cited

U.S. PATENT DOCUMENTS

2002/0192664 A1* 12/2002 Nygren et al. ..................... 435/6
2007/0231794 A1* 10/2007 Dill et al. ......................... 435/6

OTHER PUBLICATIONS

Use of Semiconductor-Based Oligonucleotide Microarrays for Influenza A Virus Subtype Identification and Sequencing Michael J. Lodes, Dominic Suciu, Mark Elliott, Axel G. Stover, Marty Ross, Marcelo Caraballo, Kim Dix, James Crye, Richard J. Webby, Wanda J. Lyon, David L. Danley, Andrew McShea Journal of Clinical Microbiology, Apr. 2006, 1209-1218.*

(Continued)

*Primary Examiner* — Krishnan S Menon
*Assistant Examiner* — Dwan A Gerido
(74) *Attorney, Agent, or Firm* — Olympic Patent Works PLLC

(57) ABSTRACT

Embodiments of the present invention are directed to efficient sensors for detecting the presence and concentration of one or more particular target molecules in solutions, air or other gasses, or otherwise present in an environment or sample. Various embodiments of the present invention provide relatively large binding constants or, equivalently, relatively small dissociation constants for binding of target biopolymers or other target molecules with complementary probes bound to, or associated with, a sensor substrate. In addition, various embodiments of the present invention increase the area of the surface of the sensor affected by binding of a target biopolymer or other target molecules to the sensor which, in turn, produces a stronger signal and greater signal-to-noise ratio for a given number or concentration of bound target biopolymers or other target molecules. In certain embodiments of the present invention, large binding constants, large signal-to-noise ratios, and strong signals are achieved by including probe molecules on the surface of the sensor directed to multiple binding sites within a target biopolymer or other target molecules, so that each bound target biopolymer or other target molecule is bound to, or associated with multiple probes.

20 Claims, 16 Drawing Sheets

(51) Int. Cl.
    *G01N 33/543*    (2006.01)
    *G01N 27/327*    (2006.01)
    *G01N 27/12*     (2006.01)
    *G01N 33/00*     (2006.01)

(52) U.S. Cl.
    CPC ..... *G01N 33/54306* (2013.01); *G01N 27/126* (2013.01); *G01N 33/0031* (2013.01)

(58) Field of Classification Search
    USPC ............ 422/82.02, 82.01; 436/501, 43; 435/6.19, 6.1, 7.1
    See application file for complete search history.

(56) References Cited

OTHER PUBLICATIONS

Sensor Array: Impedimetric Label-Free Sensing of DNA Hybridization in Real Time for Rapid, PCR-Based Detection of Microorganisms Andrei L. Ghindilis, Maria W. Smith, Kevin R. Schwarzkopf, Changqing Zhan, David R. Evans, Antonio M. Baptista, Holly M. Simon Elecrtroanalysis 2009, 21, No. 13, 1459-1468.*

* cited by examiner

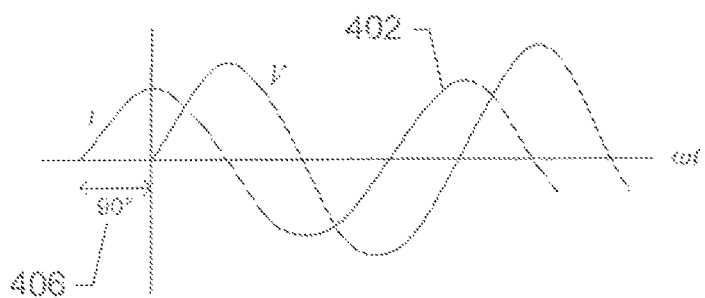
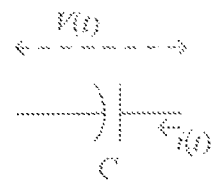
FIGURE 4A
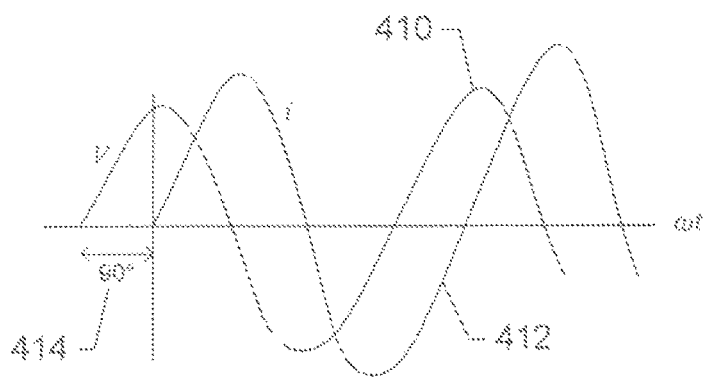
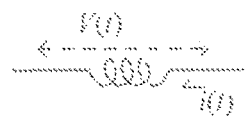
FIGURE 4B

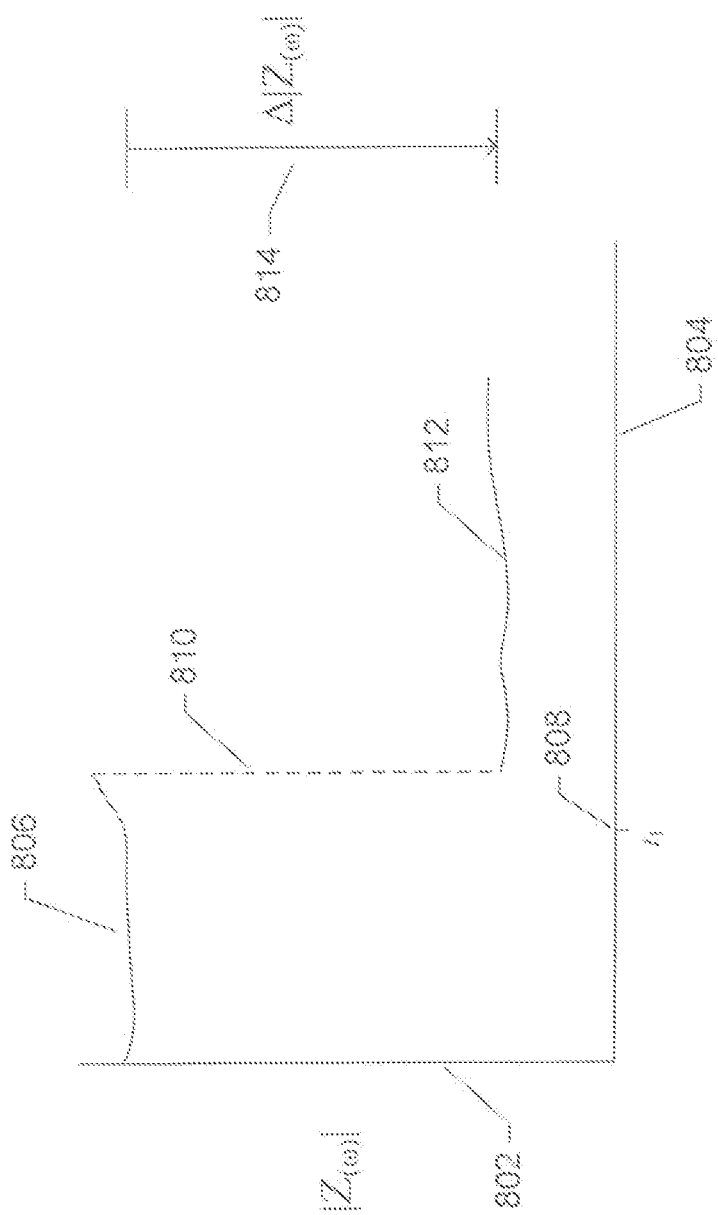

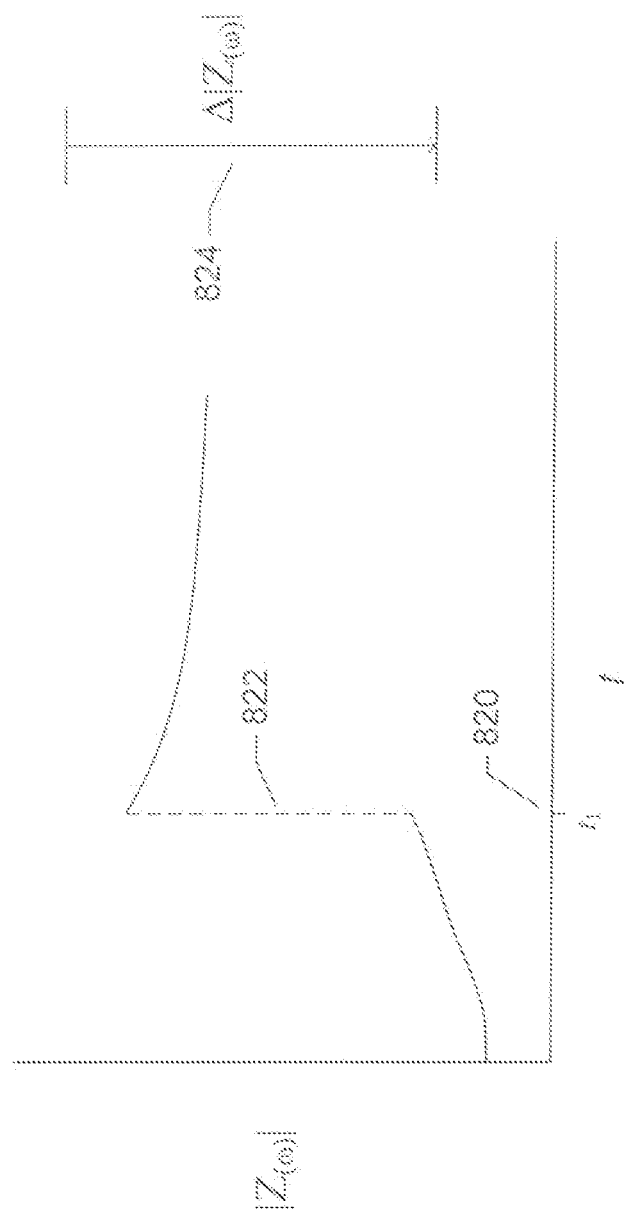

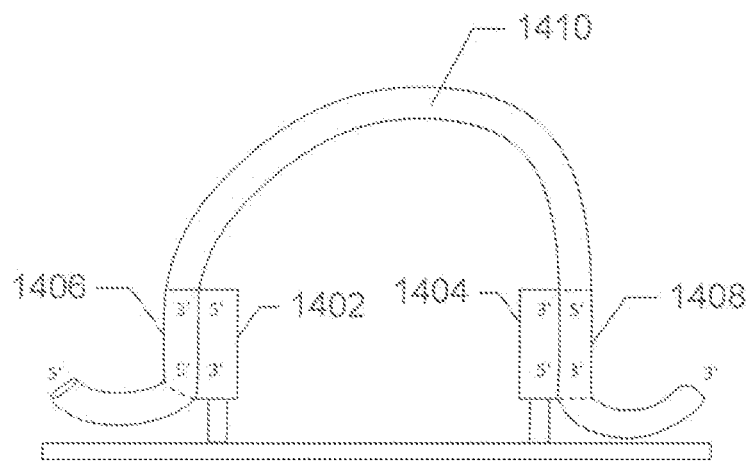
FIGURE 14A
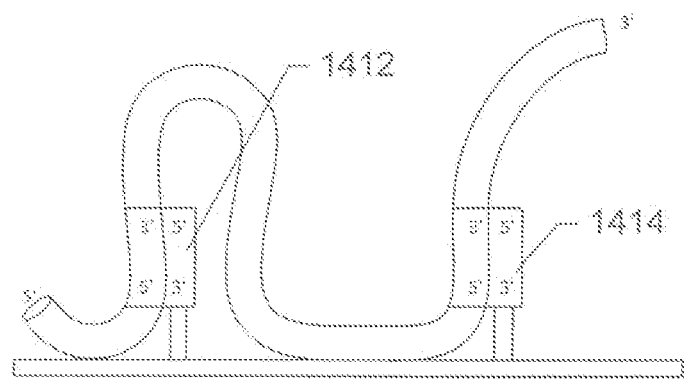
FIGURE 14B
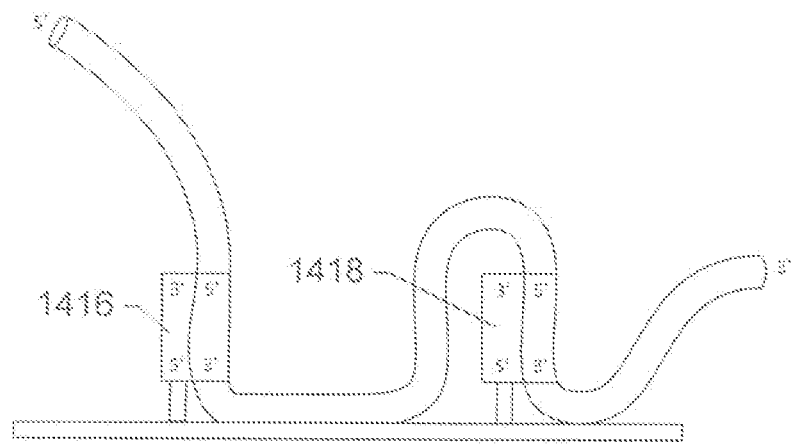

US 9,683,258 B2

EFFICIENT SENSOR FOR DETECTING AND DETERMINING THE CONCENTRATIONS OF TARGETS

TECHNICAL FIELD

The present invention is related to sensors that generate electromagnetic signals when bound to targets and, in particular, to efficient and reliable sensors that produce large signal-to-noise ratios.

BACKGROUND OF THE INVENTION

Enormous research and development efforts have been made, during the past 100 years, to develop sensors that detect the presence of target molecules, target particles, or other target objects in solutions, air or other gasses, adsorbed to surfaces, or otherwise present in an environment or sample. With the advent of modern microelectronic, sub-microelectronic, microelectromechanical, and sub-microelectromechanical fabrication technologies, a wide variety of different types of sensors have been developed for commercial use. Sensors may be macroscale devices that include arrays of microscale sensor elements, such as oligonucleotide-probe-based microarrays, or may be microscale, sub-microscale or nanoscale electromechanical, electro-optical, or optical-mechanical subcomponents of microelectromechanical devices, and microfluidic devices. A wide variety of different types of sensors are used in analytical instruments, diagnostics, and scientific instrumentation. As with many other types of technology, sensors are often characterized by various parameters of importance to researchers, designers, and manufacturers of sensor-based devices and equipment, including cost, sensitivity, specificity, viability, reusability, durability, and flexibility in application. Researchers, designers, and manufacturers of sensors and sensor-based devices and equipment continue to seek new sensor technologies that provide low-cost, reliable, durable, reusable, sensitive, and highly specific sensors that can be as broadly applied as possible to a variety of problem domains.

SUMMARY OF THE INVENTION

Embodiments of the present invention are directed to efficient sensors for detecting the presence and concentration of one or more particular target molecules in solutions, air or other gasses, or otherwise present in an environment or sample. Various embodiments of the present invention provide relatively large binding constants or, equivalently, relatively small dissociation constants for binding of target biopolymers or other target molecules with complementary probes bound to, or associated with, a sensor substrate. In addition, various embodiments of the present invention increase the area of the surface of the sensor affected by binding of a target biopolymer or other target molecules to the sensor which, in turn, produces a stronger signal and greater signal-to-noise ratio for a given number or concentration of bound target biopolymers or other target molecules. In certain embodiments of the present invention, large binding constants, large signal-to-noise ratios, and strong signals are achieved by including probe molecules on the surface of the sensor directed to multiple binding sites within a target biopolymer or other target molecules, so that each bound target biopolymer or other target molecule is bound to, or associated with, multiple probes.

BRIEF DESCRIPTION OF THE DRAWINGS

FIGS. 4A-B illustrate the relative phase changes of current and voltage waveforms in an AC electrical circuit induced by a capacitor and; inductor, respectively.

FIGS. 8A-B illustrate impedance-versus-time curves generated during introduction of a biopolymer target into the solution in which an impedance-spectroscopy-based sensor is immersed.

FIGS. 14A-F illustrate a number of particular embodiments of the present invention in the context of binding single-stranded DNA or RNA biopolymers to an impedance-spectroscopy-based sensor.

DETAILED DESCRIPTION OF THE INVENTION

Figure 1:
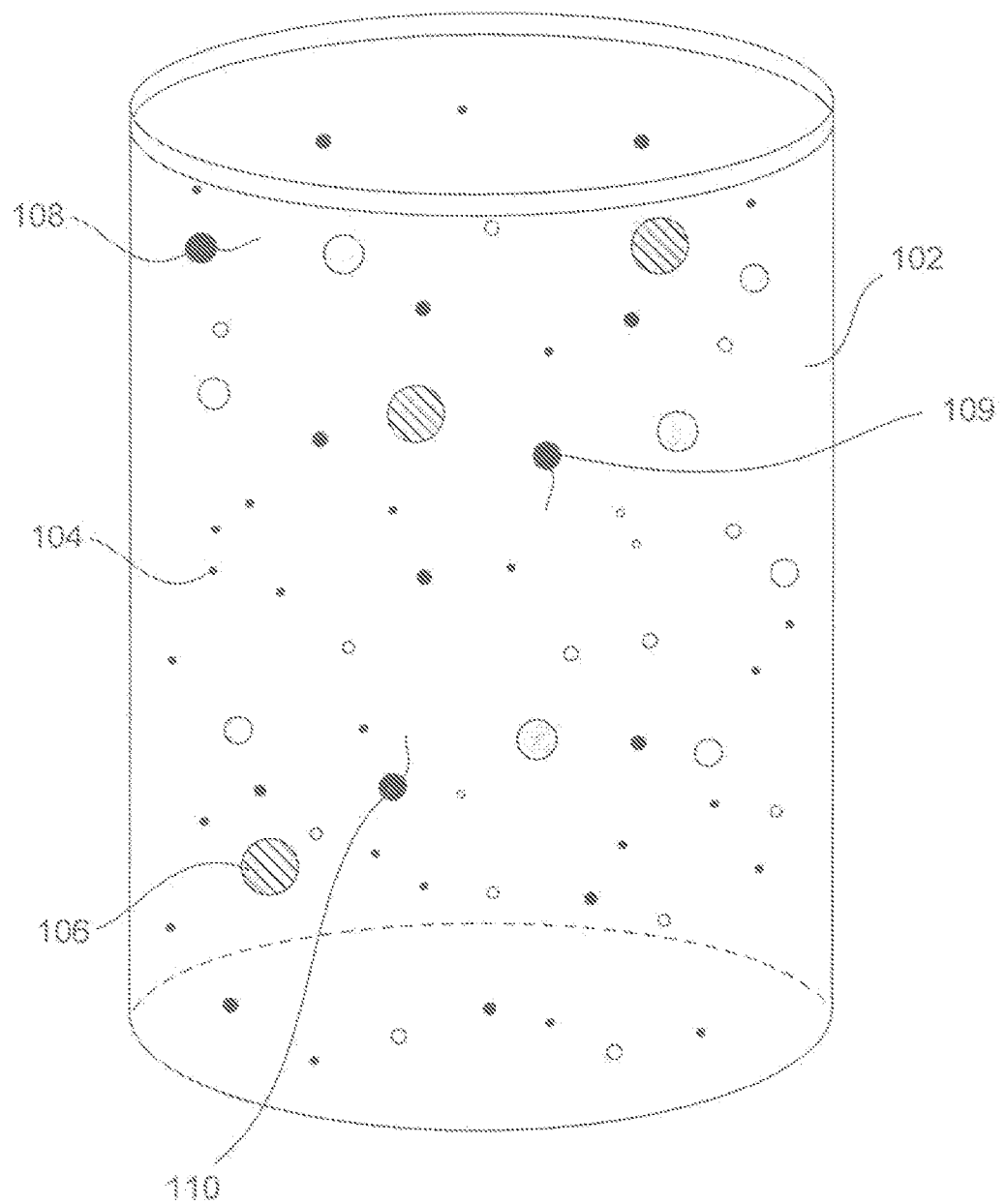
FIG. 1 illustrates a target-sensing problem domain that provides a context for a description of certain embodiments of the present invention.

FIG. 1 illustrates a target-sensing problem domain that provides a context for a description of certain embodiments of the present invention. FIG. 1 shows a small, enclosed volume 102 of a complex solution containing symbolic representations of various different small molecules and ions, such as small molecule 104, various non-target biopolymers, such as non-target biopolymer 106, as well as a target biopolymer, three instances of which 108-110 are shown in the small enclosed volume 102 illustrated in FIG. 1. FIG. 1 is not intended to provide an accurate, scale-correct rendering of an enclosed volume of a complex solution, but is instead intended to illustrate the complexity of the solution 102 as well as to introduce symbolic illustration conventions for sensor targets and for non-target entities within the solution. Considering the enclosed volume of solution to be a sample, one common problem domain constitutes determining the concentration of target entities 108-110, [t], in the small volume 102 of the solution illustrated in FIG. 1.

There are many highly accurate, mature, and generally complex technologies for determining concentrations of targets in solutions and other media. These methods include a wide variety of different types of chromatography techniques, gel electrophoresis, analytical centrifugation, fluorescent-antibody assays, and many other methods. In general, any particular method, particularly the classical biochemical methods, can be used only for a subset of the sensing problem domains. For example, many methods require a minimum volume of solution for analysis. In addition, methods generally can detect targets reliably only over particular concentration ranges. Targets may often interact with each other and/or with other molecules, particles, or other entities in the solution in ways that interfere with accurate determination of target concentration. Many methods require particular solvents, and cannot be used for other solvents. Many methods are time-consuming, expensive, and require complex instrumentation and laboratory equipment, and cannot therefore be carried out in real time or under field conditions.

For all of the above reasons, enormous effort has been undertaken, in recent years, to develop and commercialize highly specific, inexpensive, small, reliable, and sensitive sensors for detecting a wide variety of different targets in solutions, in air, adsorbed to different surfaces, substrates, and entities, and in other media and environments. The sensors may be used for environmental monitoring, biowarfare-agent detection, explosives detection, analysis of biopolymer and small-molecule solutions, detection of impurities in manufacturing quality control, and for a wide variety of additional applications, including diagnostics and scientific-research applications.

Figure 2:
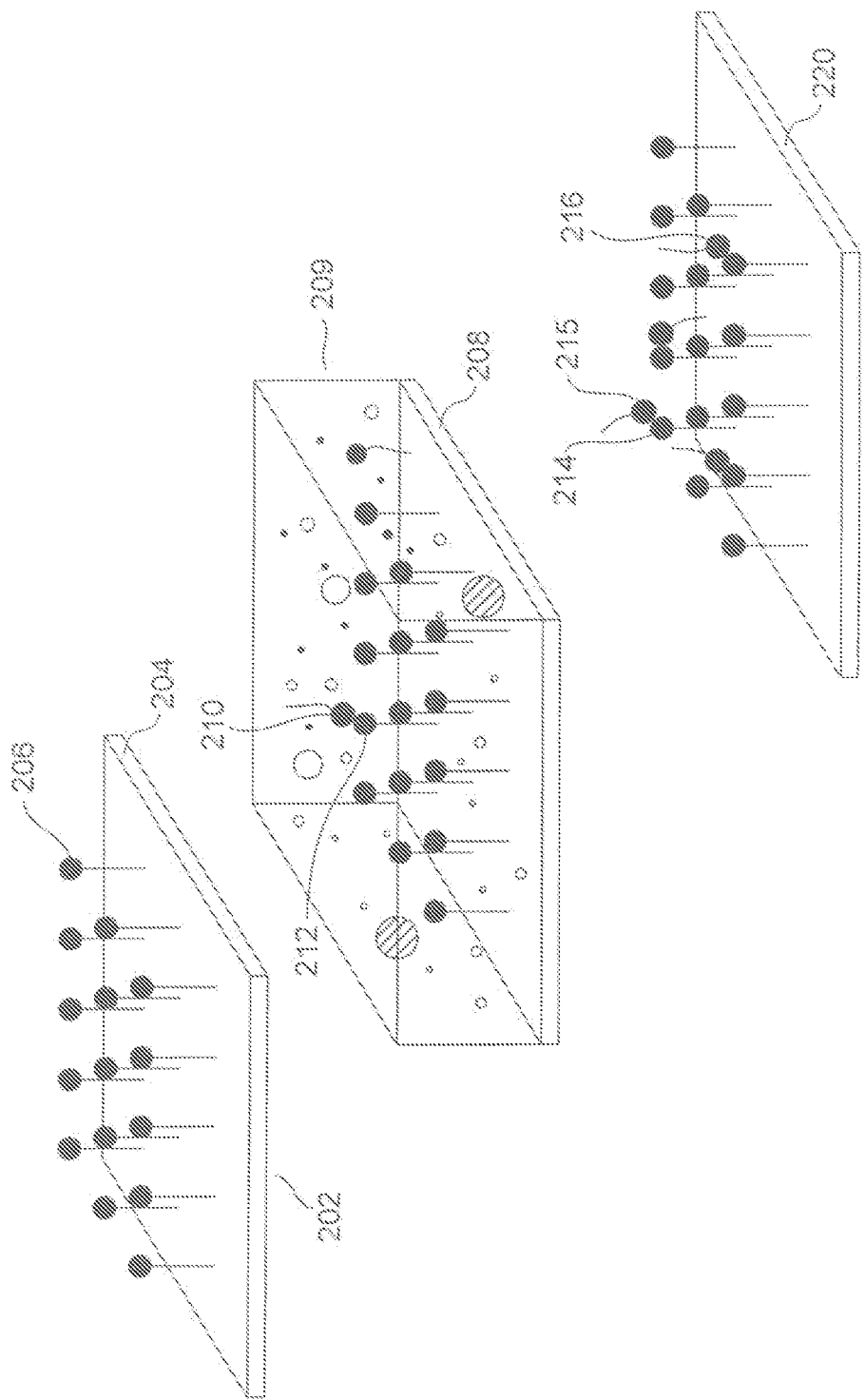
FIG. 2 illustrates a sensor-based determination of target concentration within the exemplary problem domain illustrated in FIG. 1.

In general, a sensor is a signal transducer that responds to a target concentration or target presence, in a defined environment, by generating an electromagnetic signal, including electrical current and voltage signals, optical signals, radio-frequency signals, and other types of signals that can be detected and quantitatively evaluated by electronic devices, generally microelectronic, microprocessor-controlled devices. FIG. 2 illustrates a sensor-based determination of target concentration within the exemplary problem domain illustrated in FIG. 1. In FIG. 2, a small portion 202 of a sensor is shown to include a substrate 204 and target-binding probes, such as probe 206. Different types of sensors may include different numbers of probes, from one to millions, hundreds of millions, or billions of probes that may be organized into arrays of other structures. In the following discussion, a single-probe-type sensor is discussed. For example, in the portion of the sensor 202 shown in FIG. 2, all of the probes, such as probe 206, are designed to bind, or tightly associate with, one particular type of target. However, sensors may include many different types of probes, multi-functional probes that bind to, or associate with, multiple types of targets, and various different types of chemical and/or electromechanical probes, and embodiments of the present invention are applicable to all of these different types of sensors.

In other to determine the target concentration in the exemplary-solution shown in FIG. 1, the sensor is exposed to a small volume of solution 209, shown above the sensor, substrate 208 in FIG. 2. Targets within the solution, such as target 210, randomly collide with, and bind to, probes, such as probe 212. Binding may occur by various different types of binding interactions, including ionic interactions, hydrogen bonding, Van der Waals interactions, covalent bonding, electrostatic surface attractions, and other types of binding. In many cases, binding interactions are quite specific. Targets may bind to probes with binding constants of many orders of magnitude greater than non-targets, including specific binding of biopolymer probes containing binding sites for specific small-molecule or biopolymer targets. Enzymes bind to small-molecule substrates, antibodies bind to specific antigens, and DNA-binding proteins and RNA biopolymers may bind with high specificity to particular monomer subsequences. However, useful sensors may also include less specific probes that bind less specifically to an entire class of targets.

In certain cases, after an adequate exposure time, the sample solution is washed away from the sensor surface, leaving targets bound to a certain percentage of the probes, including bound targets 214-216 in FIG. 2. In other cases, including sensors used for certain types of impedance spectroscopy, a washing or solution-substitution step is not needed. The percentage of probes bound to targets is generally representative of the concentration of target in the sample solution. Following a washing or solution-substitution step, in certain cases, or during the binding process, in other cases, the sensor is then queried, by any of various electrical or optical means, in order to detect a signal indicative of the density of bound targets on the sensor substrate, in turn indicative of target concentration in the sample solution. For example, chemiluminescent-compound-labeled biopolymer targets bound to oligonucleotide probes of a microarray can be detected by illuminating the microarray with light of a first wavelength and detecting light of a second, generally longer wavelength emitted by the chemiluminescent labels. In another example, the surface plasmon resonance technique/detects biopolymers adsorbed to surfaces by plasmon-induced changes in light reflected from the surface, including changes in reflection angles, wavelengths, and other changes in the reflected light. In microcantilever or nanocantilever transducers, mechanical bending of the nanocantilever as a result of the weight of adsorbed molecules generates a current or voltage signal that varies with the degree to which the cantilever is bent. Atomic-force microscopes move a tiny needle across a surface, positioned at a constant distance from the surface by feedback control, which generates electrical signals as the needle rises and falls as it passes over substrate atoms and adsorbed ions and molecules. As yet another examples fluorescencer-resonance-energy-transfer-based detectors may defect the proximity of different fluorescent, labels bound to targets and probes by emitting a light signal of a particular wavelength only when targets are bound to, or tightly associated with, probes so that the two different fluorophores are within some maximum distance from one another. Finally, in sensors used for impedance spectroscopy, the target-to-probe binding process is detected, while it occurs and with no washing step, by detecting a change in the impedance of an electrode at a frequency at which impedance changes are proportional to bound target density, in turn proportional to target concentration, impedance spectroscopy takes advantage of the fact that binding of target to probe changes the capacity of the electrode surface.

Figure 3:
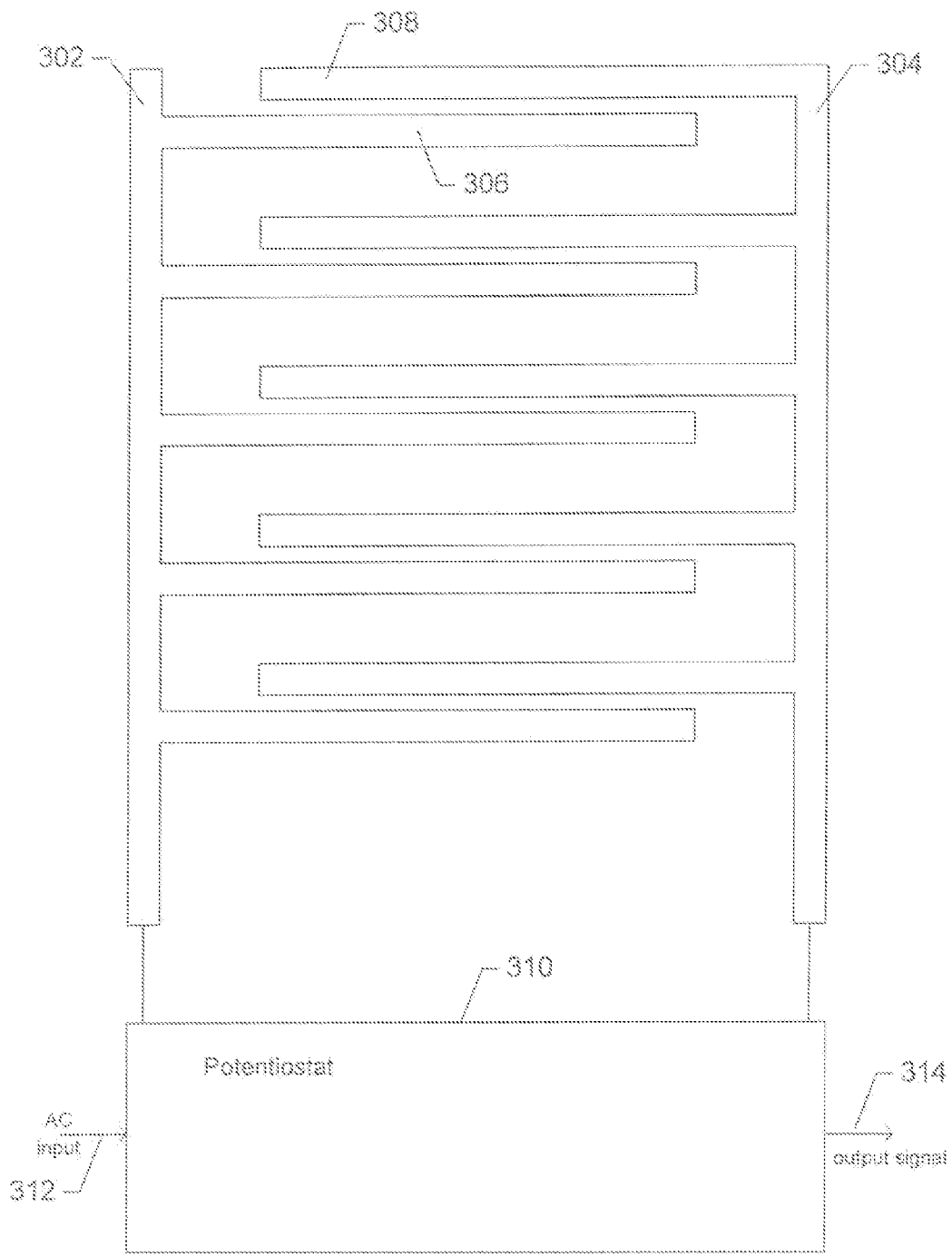
FIG. 3 illustrates an impedance-spectroscopy-based sensor.

FIG. 3 illustrates an impedance-spectroscopy-based sensor. The sensor includes a first electrode 302 and a second electrode 304, each with multiple projections, including the pair of projections or tines 306 and 308, similar to teeth of a comb, that greatly increase the area of close contact between the first electrode 302 and second electrode 304. In many impedance-spectroscopy-based sensors, the projections may have complex shapes, including-invaginations and protrusions, to further increase the area of close contact between the first and second electrodes. The electrodes are electrically coupled to a potentiostat circuit 310 which receives an alternating-current ("AC") input 312 and produces an output signal 314, the magnitude of which corresponds to the impedance of an electrical circuit within the sensor that includes the first and second electrodes 302 and 304 and a sample solution between the electrodes.

The impedance of a circuit is given by:

$$Z = \frac{V}{I}$$

where V=phasor voltage=$V_m<\theta_v$=$V_m$ cos($\omega t+\theta$)=$R_e$ $V_m e^{j(\omega t+\theta)}$ I=phasor current=$I_m<\theta_v+\phi$=$I_m$ cos($\omega t+\theta+\phi$)=$R_e$ $I_m e^{(\omega t+\theta+\phi)}$ The impedance of a circuit depends on the frequency, $\omega$, of the alternating current and alternating voltage within the circuit. Unless the circuit is purely resistive, the voltage and current phases differ by a phase angle $\phi$ that represents a combination of phase changes introduced by capacitive and inductive circuit elements. The impedance is a function of frequency to and can be expressed as:

$$Z(j\omega)=R(\omega)+jX(\omega)$$

where K is the real, or resistive component of the impedance and X is the imaginary, or reactive component of the impedance. Hie impedance is clearly a complex number, and can be written in phasor notation or an exponential notation based on Euler's equation as follows:

$$Z=|Z|<\theta_z=|Z|e^{j\phi_z}$$

As is well known in electronics, the resistance of a direct-current ("DC") circuit is expressed as:

$$R = \frac{V}{i}$$

where R is the resistance,
V is the voltage, and
i is the current.

A purely resistive component, or resistor, within either a DC or AC-circuit causes a voltage drop across the resistor, and does not induce a phase change between time-domain oscillations, or waveforms, of voltage and current in an AC circuit. By contrast, capacitors and inductors produce phase changes between the voltage and current waveforms in an AC electrical circuit. FIGS. 4A-B illustrate the relative phase changes of current and voltage waveforms in an AC electrical circuit induced by a capacitor and inductor, respectively. As shown in FIG. 4A, the phase of the current waveform 402 leads the phase of the voltage waveform 404 by 90° 406 within a capacitor. As shown in FIG. 4B, the voltage waveform 410 leads the current waveform 412 in phase by 90° 414 within an inductor. The impedance of an AC circuit includes a purely resistive component R, a capacitive reactance component $X_C$, and an inductive reactant component $X_L$:

$$R = \frac{V\angle\theta}{I\angle\theta} = R\angle 0°$$

$$X_C = \frac{V\angle\theta}{I\angle\theta+90°} = \frac{|V|}{|I|}\angle-90° = \frac{1}{\omega C}\angle-90°$$

$$X_L = \frac{V\angle\theta+90°}{I\angle\theta} = \frac{|V|}{|I|}\angle 90° = \omega L\angle 90°$$

The total impedance of an AC circuit is computed from the impedance of each circuit element, and generally includes all three of the purely, resistive, capacitive reactance, and inductive reactance components. Impedance is the AC analog of resistance in DC circuits.

Figure 5:
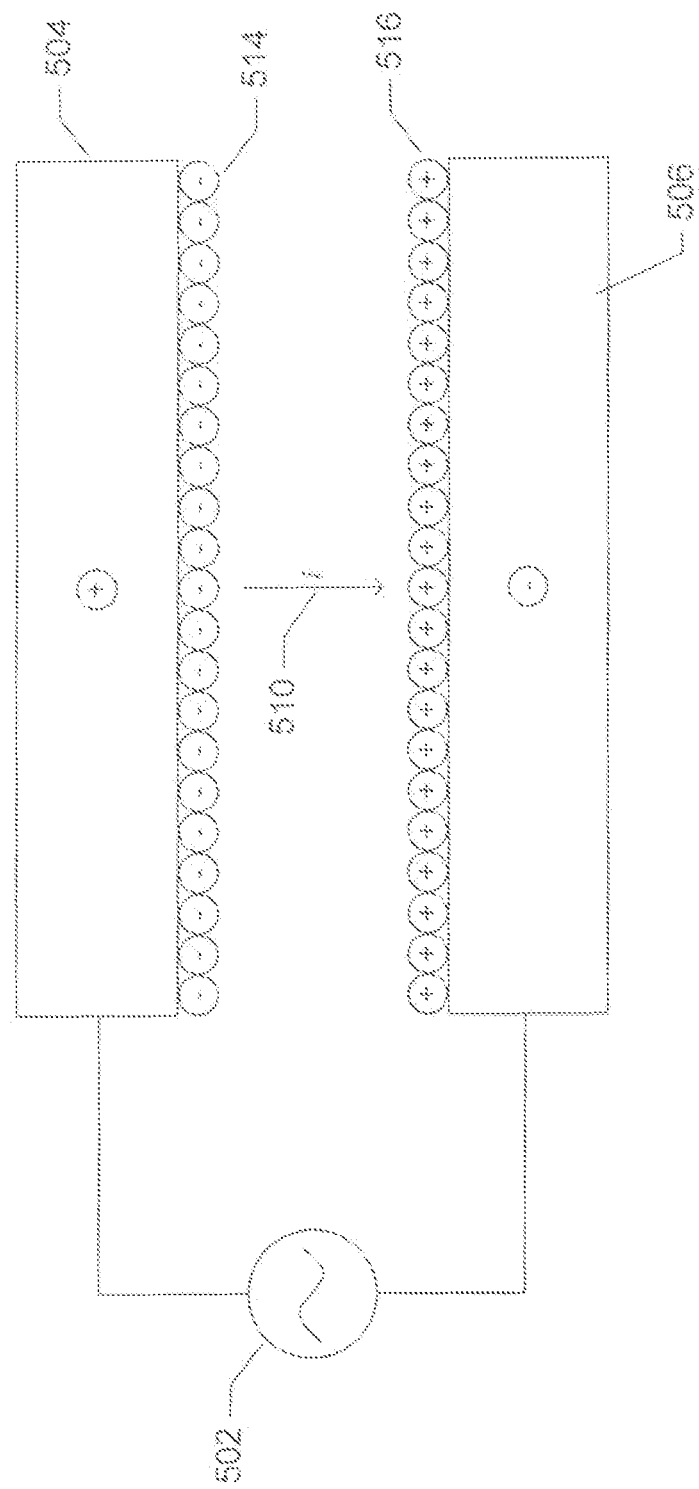
FIG. 5 illustrates a simple form of the impedance-spectroscopy-based sensor discussed above with reference to FIG. 3.

FIG. 5 illustrates a simple form of the impedance-spectroscopy-based sensor discussed above with reference to FIG. 3. The impedance-spectroscopy-based sensor includes an alternating current source 502, a first electrode 504, and a second electrode 506. Current flows between the first electrode 504 and second electrode 506, as indicated by arrow 510 in FIG. 5, through the solution or medium between the two electrodes. The first electrode 504, shown as the positive electrode, or cathode, in FIG. 5, accumulates a layer of negatively charged dons and/or polarizable solutes 514 and the negatively charged electrode 506, or anode, accumulates a layer of positively charged ions and/or polarizable solutes. This accumulation of ions and polarizable solutes on the surface of the electrode, as well as probes bound to, or associated with, the surface of the electrode produces a capacitance.

Figure 6:
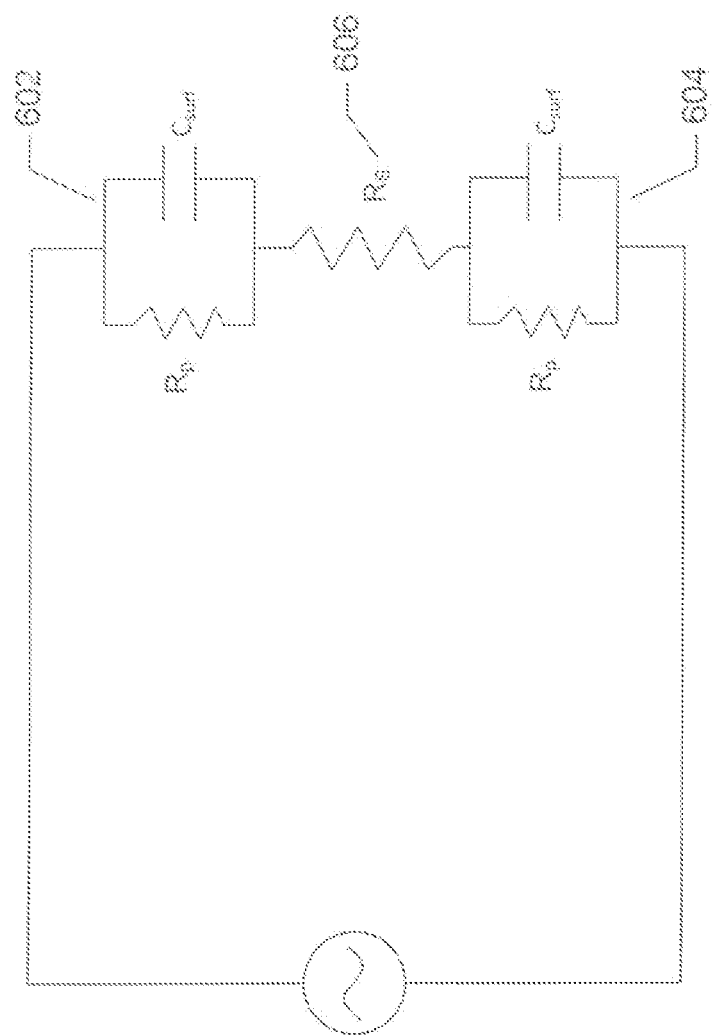
FIG. 6 shows the equivalent circuit for the sensor shown in FIG. 5.

The sensor shown in FIG. 5 can be modeled by an equivalent circuit. FIG. 6 shows the equivalent circuit for the sensor shown in FIG. 5. The first electrode and layer of bound ions and the polarizable solutes is modeled by a resistor, which models polarization-induced resistance, in parallel with a capacitor 602, and the second electrode (506 in FIG. 5) is also modeled by a resistor in parallel with a capacitor 604. The solution path of the current (510 in FIG. 5) is modeled by a solution resistance 606. The capacitor $C_{surf}$ in each capacitor/resistor subcircuit that models each of the first and second electrodes, 602 and 604, may be further modeled as a serial pair of capacitors $C_{sm}$ and $C_{dl}$ representing the capacitance resulting from modification of the surface of the electrode by covalent attachment or association of probe molecules to the electrode and the capacitance due to a layer of ions and/or polarizable solutes bound to the surface of the electrode:

$$C_{surf} = \frac{C_{sm}C_{dl}}{C_{sm}+C_{dl}}$$

The surface-modification capacitance $C_{sm}$ is often modeled as:

$$C_{sm}=\epsilon_r\epsilon_o A/t$$

where $\epsilon_o$ is the electrical permittivity;
$\epsilon_r$ is the relative permittivity;
A is the electrode area; and
t is the thickness of the probe layer.

The impedance due to the double-layer capacitance, $C_{dl}$, may be modeled as:

$$Z_{dl} \cong \frac{1}{(j\omega C_{dl})^m}$$

where m ranges from 0.5 to 1.0. In other words, the double-layer capacitance, $C_{dl}$, introduces a phase change different from 90°.

Figure 7:
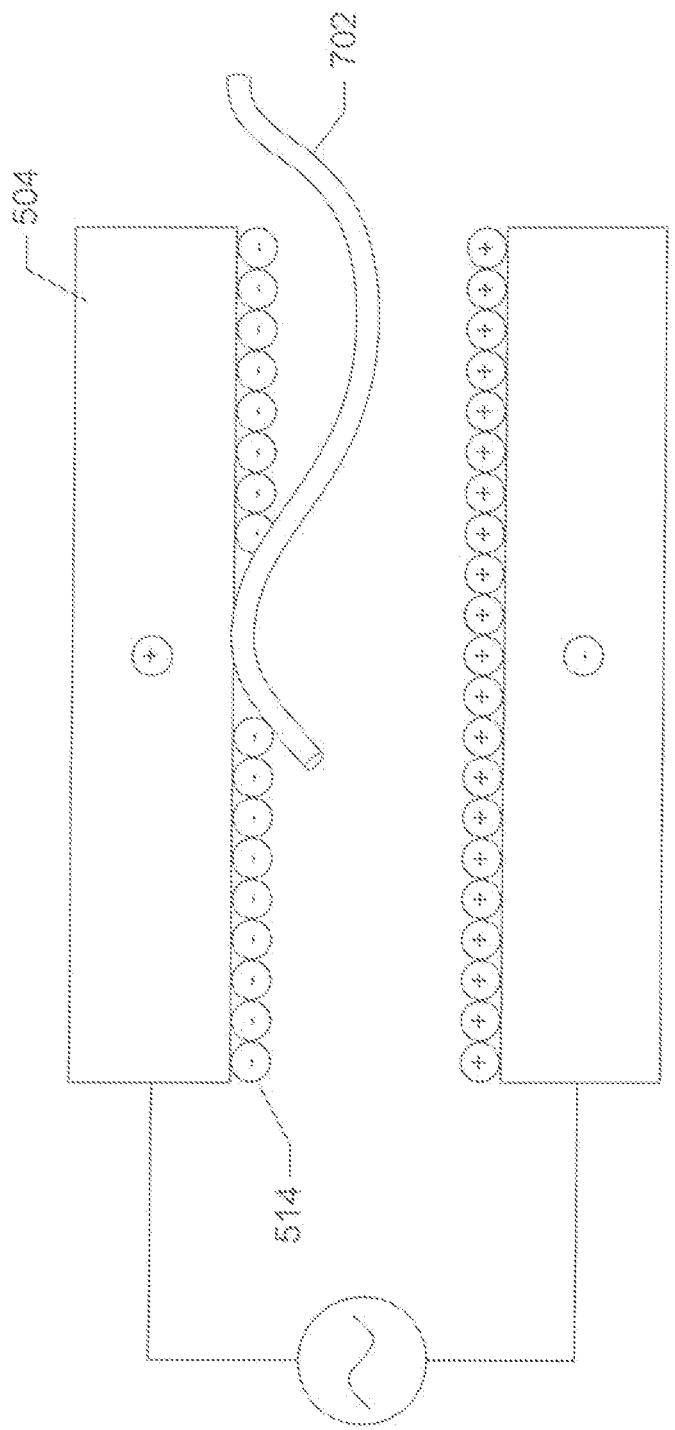
FIG. 7 illustrates the sensor shown in FIG. 5 with a bound target biopolymer.

FIG. 7 illustrates the sensor shown in FIG. 5 with a bound target biopolymer. In FIG. 7, the target biopolymer 702 is bound to the first electrode, or cathode 504. Binding of the target biopolymer 702 may displace or reorganize a portion of the layer of ions and polarizable solutes 514, and thus change the value of $C_{dl}$ for the electrode. In addition, binding of the target biopolymer may change the surface-modification capacitance $C_{sm}$. In certain cases, the resistance $R_p$, or polarization resistance, shown in FIG. 6 in parallel with the capacitor in each resistor/capacitor model for an electrode, may also be affected by binding the target biopolymer. Many different hypotheses and theories have been proposed for specific physical changes in the electrode surfaces and electrode-surface environments due to target-biopolymer binding to probe molecules on the surface of the sensor, but, in general, definitive physical explanations have so far eluded researchers. However, whatever the exact physical chemical processes involved, binding of target biopolymers to impedance-spectroscopy-based-sensors, as shown in FIG. 7, produces detectable, changes in the impedance of the electrode circuit, modeled by the equivalent circuit shown in FIG. 6.

FIGS. 8A-B illustrate impedance-versus-time curves generated during introduction of a biopolymer target into the solution in which an impedance-spectroscopy-based sensor is immersed. Both FIGS. 8A-B use the same illustration conventions, next discussed with reference to FIG. 8A. In FIG. 8A, the magnitude of the impedance $|Z(\omega)|$ of the sensor circuit at a particular selected AC frequency, $\omega$, is plotted with respect to the vertical axis 802 and time is plotted with respect to the horizontal axis 804. As shown in FIG. 8A, the initial impedance of the sensor, in the absence of the target biomolecule, is represented by a first portion of the impedance versus time curve 806. After the introduction of the target biopolymer into the solution in which the sensor is immersed, at time $t_1$ 808, the impedance slightly rises and then falls precipitously, as represented by a dashed line 810, to a relatively smaller impedance value 812. Thus, binding of the target biopolymer results in a decrease in the impedance of the sensor circuit 814. Because impedance is inversely related to the capacitive reactance of the circuit, the drop in impedance may result from an increase in one or both of $C_{sm}$ and $C_{dl}$ for the electrode to which the target biopolymer binds, a decrease in the polarization resistance $R_p$ for the electrode to which the target biopolymer binds, or a combination of a decrease in capacitance and an increase in resistance of the electrode to which the target biopolymer binds. In other cases, as shown in FIG. 8B, introduction of the target biopolymer at time $t_1$ 820 results in a steep increase, represented by vertical dashed line 822, in the impedance of the sensor circuit. The increase in impedance may result from a decrease in one or both of $C_{sm}$ and $C_{dl}$ for the electrode to which the target biopolymer binds, an increase in the polarization resistance $R_p$ for the electrode to which the target biopolymer binds, or a combination of a decrease in capacitance and an increase in resistance of the electrode to which the target biopolymer binds. In both cases, the magnitude of a change in impedance, upon binding of target to the electrode surface, may be functionally related to the number or density of bound target, in turn proportional to the concentration of the target in a sample solution to which the sensor is exposed.

Figure 9:
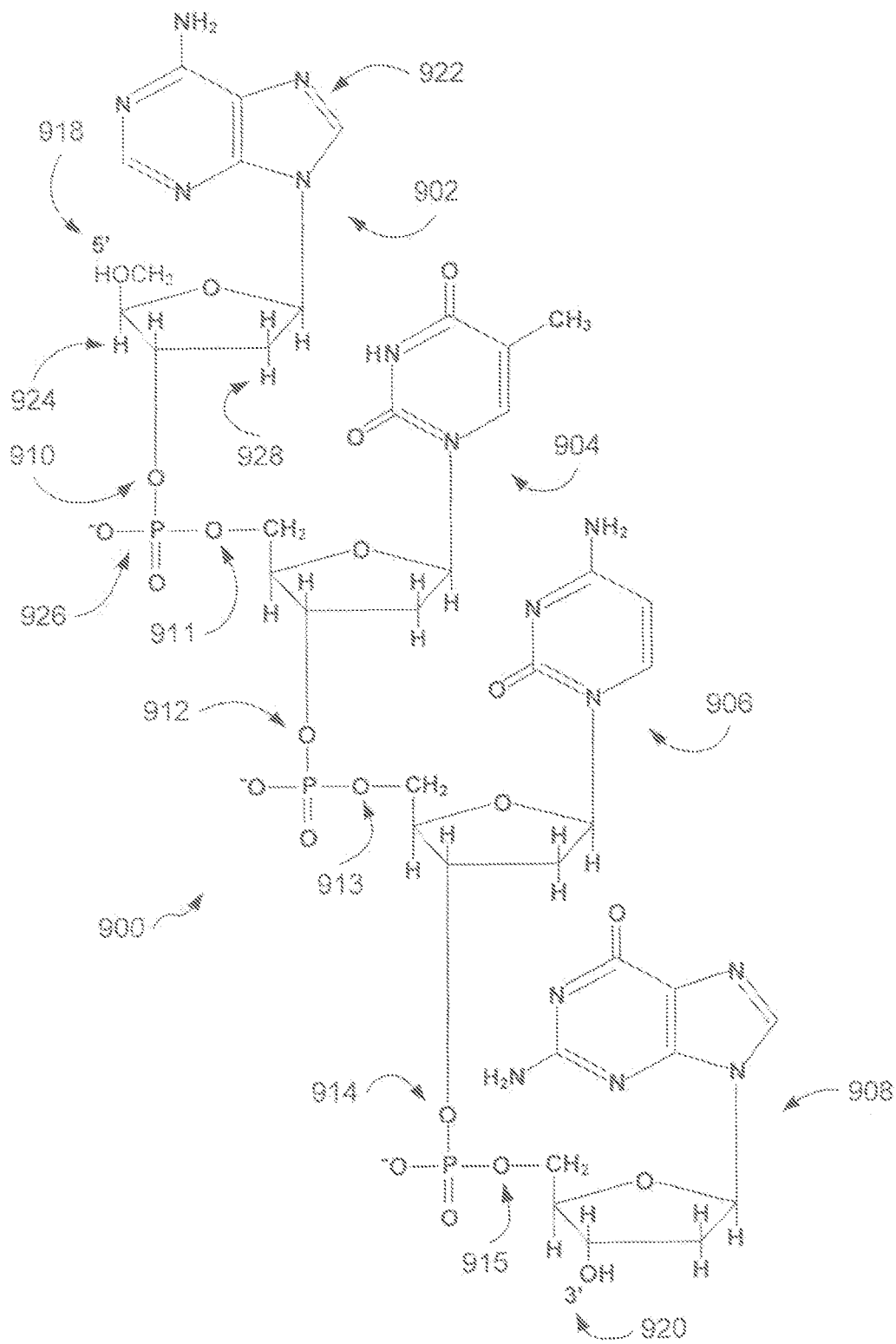
FIG. 9 illustrates a short oligonucleotide.

FIG. 9 illustrates a short oligonucleotide. The oligonucleotide is composed of the following subunits: (1) deoxyadenosine 902; (2) deoxy-thymidine 904; (3) deoxy-cytosine 906; and (4) deoxy-guanosine 908. When phosphorylated, subunits of deoxyribonucleic-acid ("DNA") and ribonucleic-acid ("RNA") polymers are called "nucleotides" and are linked together through phosphodiester bonds 910-915 to form DNA and RNA polymers. A linear DNA molecule, such as the oligomer shown in FIG. 9, has a 5' end 918 and a 3' end 920. A DNA polymer can be chemically characterized by writing, in sequence from the 5' end to the 3' end, the single letter abbreviations for the nucleotide subunits that together compose the DNA polymer. For example, the oligomer 900 shown in FIG. 9 can be chemically represented as "ATCG." A DNA nucleotide comprises a purine or pyrimidine base (e.g. adenine 922 of the deoxy-adenylate nucleotide 902), a deoxy-ribose sugar (e.g. deoxy-ribose 924 of the deoxy-adenylate nucleotide 902), and a phosphate group (e.g. phosphate 926) that links one nucleotide to another nucleotide in the DNA polymer.

The DNA polymers that contain the organization information for living organisms occur in the nuclei of cells in pairs, forming double-stranded DNA helixes. One polymer of the pair is laid out in a 5' to 3' direction, and the other polymer of the pair is laid out in a 3' to 5' direction. The two DNA polymers in a double-stranded DNA helix are therefore described as being anti-parallel. The two DNA polymers, or strands, within a double-stranded DNA helix are bound to each other through attractive forces including hydrophobic interactions between stacked purine and pyrimidine bases and hydrogen bonding between purine and pyrimidine bases, the attractive forces emphasized by conformational constraints of DNA polymers. Because of a number of chemical and topographic constraints, double-stranded DNA helices are most stable when deoxy-adenylate subunits of one strand hydrogen bond to deoxy-thymidylate subunits of the other strand, and deoxy-guanylate subunits of one strand hydrogen bond to corresponding deoxy-cytidilate subunits of the other strand. The two strands have complementary sequences.

Figure 10A:
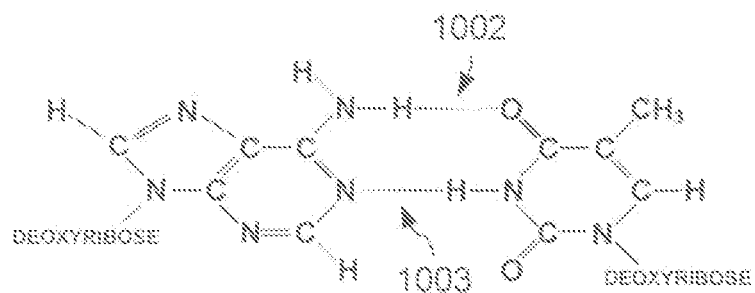
FIGS. 10A-B illustrate the hydrogen bonding between the purine and pyrimidine bases of two anti-parallel DNA strands.
Figure 10B:
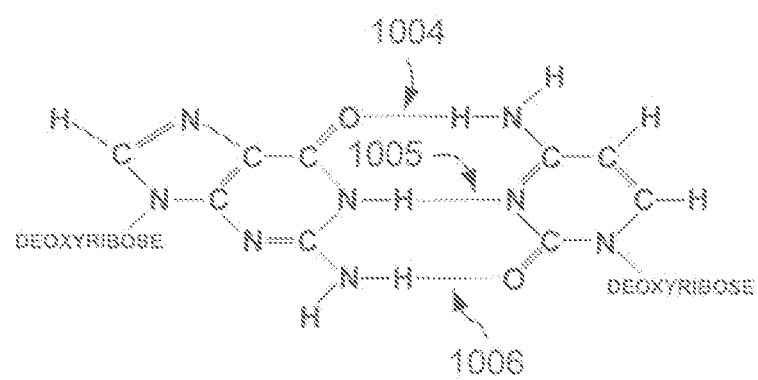
Figure 11:
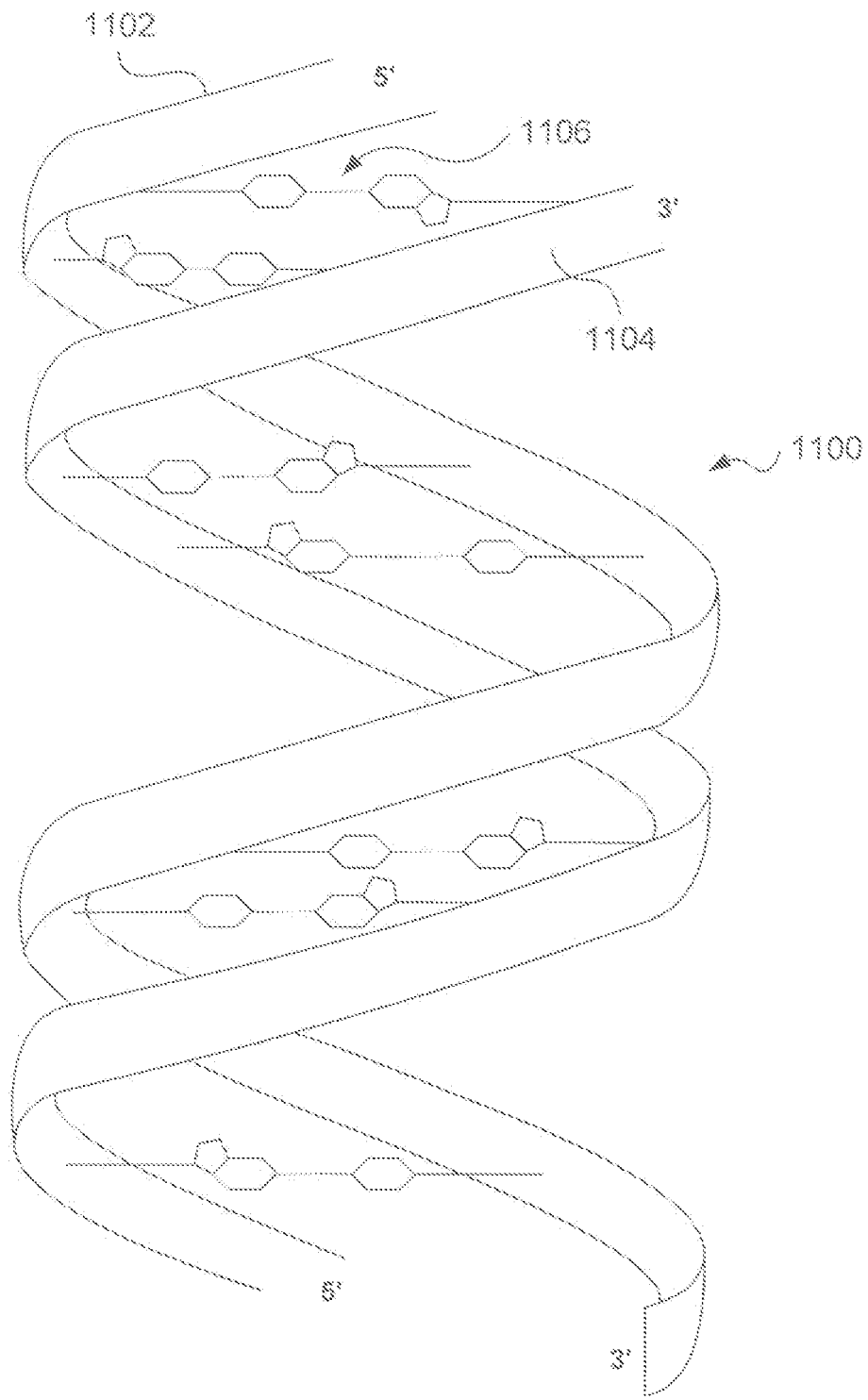
FIG. 11 illustrates a short section of a DNA double helix comprising a first strand and a second, anti-parallel strand.

FIGS. 10A-B illustrate the hydrogen bonding between the purine and pyrimidine bases of two anti-parallel DNA strands, AT and GC base pairs, illustrated in FIGS. 10A-B, are known as Watson-Crick ("WC") base pairs. Two DNA strands linked together by hydrogen bonds forms the familiar helix structure of a double-stranded DNA helix. FIG. 11 illustrates a short section of a DNA double helix comprising a first strand and a second, anti-parallel strand.

In the following examples of embodiments of the present invention, an impedance-spectroscopy-based sensor is used to detect the presence of single-stranded DNA or RNA in a solution and to quantify the concentration of the target single-stranded DNA or RNA biopolymer, which is proportional to a change in impedance of the sensor, as discussed above with reference to FIGS. 8A-B, when the target single-stranded DNA or RNA biopolymer binds to probes bound to an electrode surface. The probe molecules, in these examples, arc oligonucleotides complementary to a subsequence of the target single-stranded RNA or DNA and are covalently bound to the electrode surface by any of various functionalization techniques. For example, an oligonucleotide can be functionalized, at either the 3' or 5' end, to include a sulfhydryl group that covalently binds to Au at the surface of gold or gold-containing nanoparticles. One exemplary sulfhydryl-functionalized oligonucleotide includes a 6-mercapto-hexanol with the hexanol hydroxyl oxygen replacing a phosphate oxygen in the 5'-terminal phosphate group of the oligonucleotide. The oligonucleotide probes may be varied in length and sequence to provide complementary binding to complementary subsequences of the target biomolecule of a desired thermodynamic stability. In general, the strength of binding the target biomolecule to a complementary probe oligonucleotide is proportional to the length of the complementary oligonucleotide.

Figure 12:
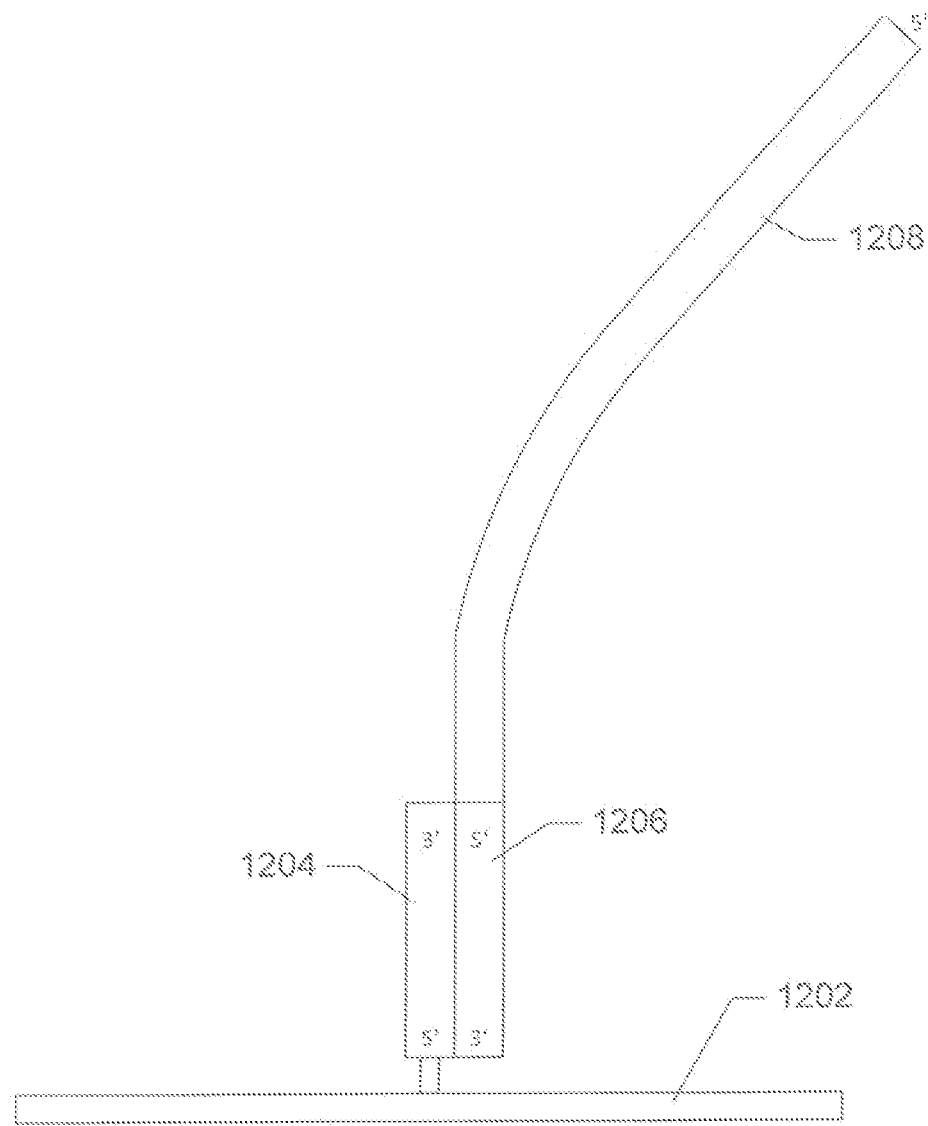
FIG. 12 illustrates an approach generally used for binding target molecules to impedance-spectroscopy-sensor electrodes.

FIG. 12 illustrates an approach generally used for binding target molecules to impedance-spectroscopy-sensor electrodes. The electrode surface 1202 is generally functionalized to contain a single probe oligonucleotide 1204 complementary to a single binding site 1206 within the target biopolymer 1208. In certain applications, the sensor electrode may be functionalized to contain two or more types of oligonucleotide probes, but in currently available technologies, each of the different types of probe is designed to bind to a different target biopolymer, and each target biopolymer binds to a single probe. This technology provides very specific binding of target biopolymers to sensors, and has been used for a variety of extremely sensitive and useful analysis and diagnostic techniques. However, in many cases, particularly when the concentration of target biopolymer in sample solutions is extremely low, the change in sensor impedance, in the case of impedance-spectroscopy-based sensors, may be of insufficient magnitude to generate signal-to-noise ratios adequate for reliable and accurate quantification of extremely low concentration of target biopolymers in sample solutions. Even in the case of more concentrated sample solutions, the signal-to-noise ratios may be nonetheless inadequate, due to various different modes of non-specific binding or association of non-target biopolymers and solutes to the electrode surfaces.

Figure 13A:
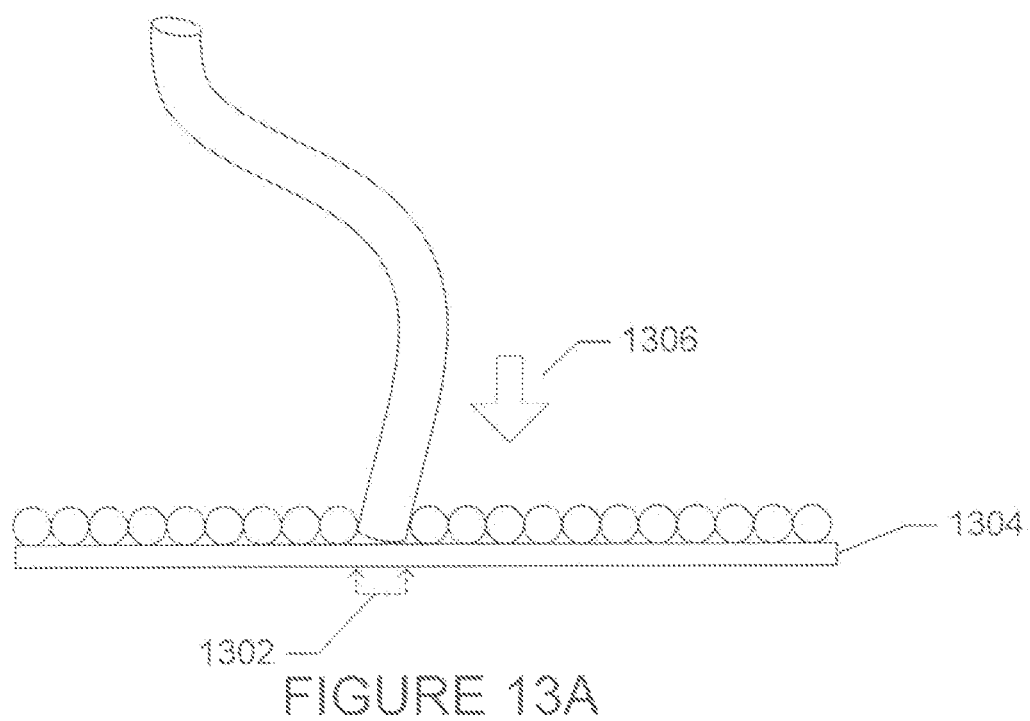
FIGS. 13A-B illustrate the approach of certain embodiments of the present invention to provide efficient impedance-spectroscopy-based sensors.
Figure 13B:
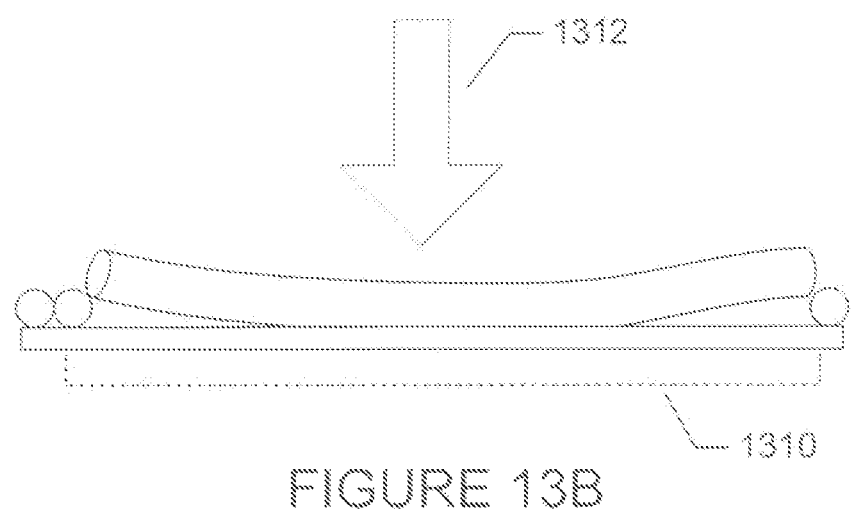

FIGS. 13A-B illustrate the approach of certain embodiments of the present invention to provide efficient impedance-spectroscopy-based sensors. The approach illustrated in FIGS. 13A-B provides efficient impedance-spectroscopy-based sensors that generate desirable signal-to-noise ratios even for very low concentrations of target biopolymers in sample solutions and in the presence of non-specific binding of non-target biopolymers and other solutes to the sensor. FIG. 13A shows the type of target-biopolymer binding encountered in many currently available sensors, as also shown in FIG. 12A. In these cases, generally only a relatively small area 1302 of the electrode surface 1304 is affected by biopolymer binding, and the force or strength of binding, represented by arrow 1306, is relatively-low. Embodiments of the present invention seek to alter binding of the target biopolymers, as shown in FIG. 13B, to increase the area of the surface of the electrode 1310 modified or affected by binding of the target biopolymer and to increase the strength of binding 1312, or magnitude of the binding constant, without irreversibly attaching the target biopolymer to the electrode surface, and thus rendering the sensor useful for only a single measurement or analysis.

Figure 14D:
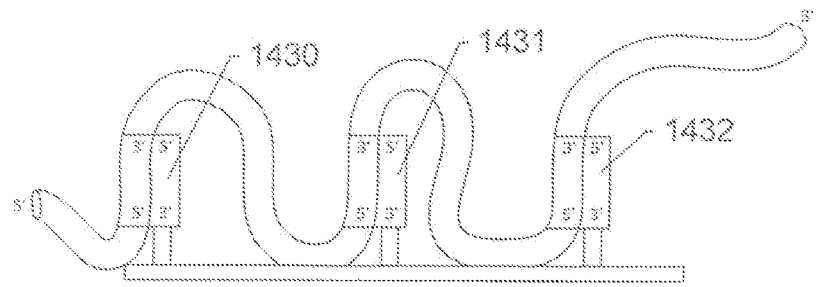

FIGS. 14A-F illustrate a number of particular embodiments of the present invention in the context of binding single-stranded DNA or RNA biopolymers to an impedance-spectroscopy-based sensor; in a first set of embodiments, shown in FIGS. 14A-C, the sensor electrode surface is functionalized with two different probe oligonucleotides complementary to two different subsequences within the target biopolymer. In this case, each target biopolymer is bound to two different probes, increasing the strength of binding of the target biopolymer to the electrode surface as well as the surface area of the electrode affected by target-biopolymer binding. In FIG. 14A, two oligonucleotide probes of opposite polarity 1402 and 1404 bind to two complementary subsequences 1406 and 1408, respectively, of the target biopolymer 1410. The first oligonucleotide probe 1402 is bound to the electrode at its 3' end, and the second oligonucleotide probe 1414 is bound to the electrode at its 5' end. In an embodiment shown in FIGS. 14B and C, the two different probe oligonucleotides have identical polarities, in FIG. 14B, the two oligonucleotide probes 1412 and 1414 are attached to the electrode surface through their 3' ends, and in FIG. 14C, the two different oligonucleotide probes 1416 and 1418 are attached to the electrode substrate through their 5' ends.

Figure 14E:
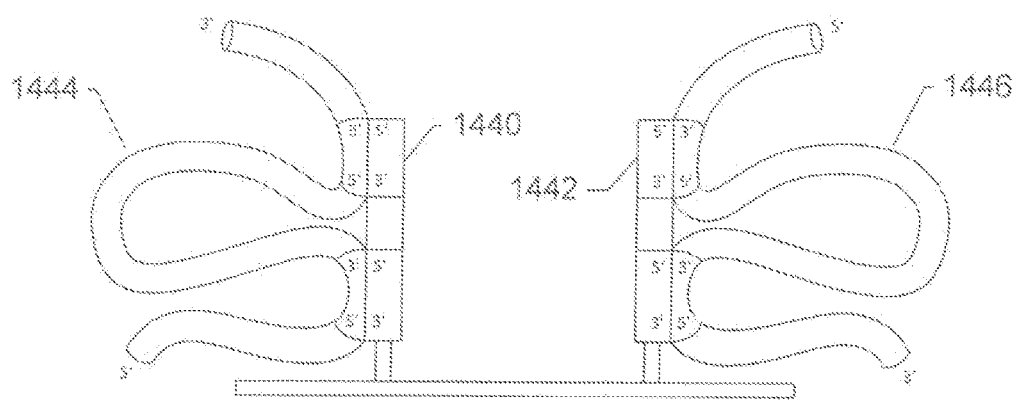

As shown in FIG. 14D, three or more different probes can be bound to, or associated with, the electrode surface to bind to three or more different subsequences within a target biomolecule. In FIG. 14D, three different probes 1430-1432 all have the same orientation, but in alternative embodiments of the present invention, the three or more probes may have any of all possible combinations of orientations. In the embodiment shown in FIG. 14E, each of two different probes 1440 and 1442 contains two subsequences complementary to two different subsequences on each target biopolymer. As shown in FIG. 14E, this results in a bound target biopolymer forming a hairpin loop 1444 and 1446. In alternative embodiments of the present invention, each probe may contain three or more subsequences targeted to three or more complementary subsequences of a particular target biopolymer, resulting in two or more hairpin loops.

Figure 14F:
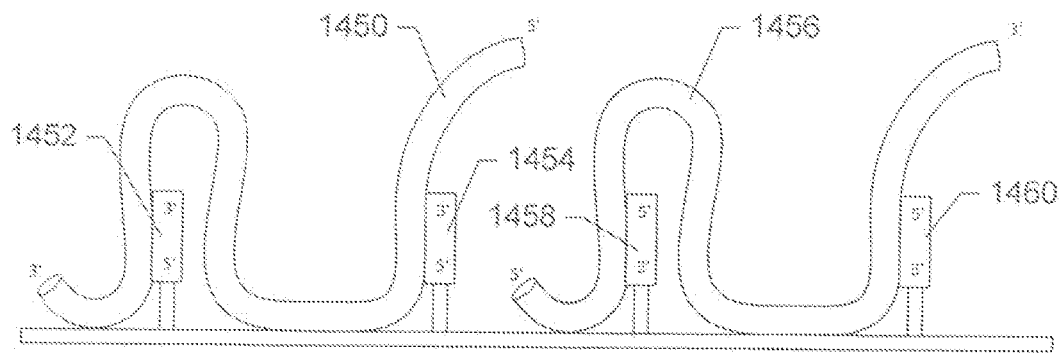

As shown in FIG. 14F, the multi-probe embodiments of FIGS. 14A-E can be extended to include pairs, triples, or higher-order sets of probes targeting each strand of a double-stranded DNA or RNA target biopolymer. In FIG. 14F, a first strand 1450 of a double-stranded DNA polymer is shown bound to probe oligonucleotides 1452 and 1454, while the complementary strand 1456 of the double-stranded DNA target biopolymer is bound to oligonucleotide probes 1458 and 1460. An electrode functionalized with two sets of oligonucleotide probes, each set targeting a different strand of a double-stranded target biopolymer is particularly effective when the sample solution is exposed to heat, or when the ionic strength of the sample solution is increased to melt double-stranded target biopolymers prior to exposure of the sample solution to the electrode surface.

Functionalization of electrode surfaces to produce multiple probe oligonucleotides targeting multiple complementary subsequences in each target biopolymer can be carried out stochastically or by various nano-fabrication and macromolecular-chemistry techniques. In a stochastic functionalization, the electrode surface may be exposed to mixture of two or more functionalized probe oligonucleotides. Alternatively, the electrode can be first exposed to a solution of an activated oligonucleotide probe of a first type at sufficient concentration to produce a desired density of the first type of oligonucleotide probes on the electrode surface. The desired density provides a remaining, unfunctionalized sub-electrode surface for binding a second, activated oligonucleotide probe. The second oligonucleotide probes bind among the already-bound first oligonucleotide probes, so that pairs of first and second probes are collocated to allow for multiple-probe binding to individual target biopolymers. Alternatively, a first activated oligonucleotide probe may be initially bound to a bulky, complementary masking molecule prior to binding to the electrode surface. Following binding of the first oligonucleotide probe with bound masking molecule, the temperature of the solution is changed, or the ionic strength of the solution is altered, to dissociate the masking molecule from the bound oligonucleotide probe in order to leave spaces in the surface of the electrode for binding a second type of oligonucleotide probe. In yet an alternative strategy, oligonucleotide probes may be bound to two-dimensional DNA frameworks that provide highly ordered arrangements and spacings of various types of oligonucleotide probes, and the oligonucleotide probes can then be bound to the electrode substrate, following which the two-dimensional DNA framework can be dissociated from the bound oligonucleotide probes and removed from the solution by washing.

Although the present invention has been described in terms of particular embodiments, it is not intended that the invention be limited to these embodiments. Modifications will be apparent to those skilled in the art. For example, while oligonucleotide probes have been discussed in the context of sensors that detect RNA and DNA target biopolymers, alternative embodiments of the present invention may provide multiple probes, each targeting a different binding site within other types of target biopolymers. In general, in order to provide sufficiently strong binding to produce a strong impedance-change signal and large signal-to-noise ratio, but to prevent irreversible binding of target biopolymers to the functionalized electrode surface, the binding constants, or dissociation constants, that characterize each of multiple probe molecules targeting different binding sites of a target biopolymer should be similar, so that the means employed to associate target biopolymers from the sensor following analysis developed for single-probe-per-target-biopolymer techniques can be employed for the multiple-probe sensors that represent embodiments of the present invention. When, for example, all of the multiple types of probe oligonucleotides target different subsequences within a target DNA or RNA biopolymer have similar melting temperatures, the DNA or RNA target biopolymers can be removed or dissociated from the electrode surface using melting temperatures and times similar to those used to remove target biopolymers found through a single oligonucleotide probe to an electrode surface. In additional embodiments of the present invention, the probe molecules may be multiply functionalized and multiply linked to the electrode surface in order to position bound target biopolymers closely and securely to the electrode substrate. Multiple pairs or larger sets of probes directed to multiple targets may be employed to provide a sensor responsive to two or more targets.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purpose of illustration and description. They are not intended to be exhaustive or to limit the invention to the precise forms disclosed. Many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

The invention claimed is:

1. A sensor comprising:
   a substrate;
   a signal-generation component coupled to the substrate that produces a sensor signal; and
   two or more types of probes associated with, or bound to, the substrate, each type of probe binding to a different binding site of a target, so that, when the sensor is exposed to the target, the target is bound to two or more probes at two or more binding sites to produce a change, in one or more physical characteristics of the substrate, probes, and/or other substrate-associated entities, that is detected by the signal-generation component, which generates a corresponding sensor signal.

2. The sensor of claim 1
   wherein the substrate is the surface of an electrode;
   wherein the one or more physical characteristics are modeled as a capacitance associated with the substrate, probes, and/or other substrate-associated entities; and
   wherein the signal-generation component detects a change in impedance of a sensor circuit that includes the electrode as a circuit component.

3. The sensor of claim 1
   wherein the probes are oligonucleotides bound to the substrate; and
   wherein the target is a nucleotide polymer with multiple subsequences, each subsequence complementary to a different oligonucleotide probe.

4. The sensor of claim 3 wherein:
   a first oligonucleotide probe with a first sequence and a second oligonucleotide probe with a second sequence are covalently bound to the substrate, the first sequence complementary to a first subsequence of the target and the second sequence complementary to a second subsequence of the target.

5. The sensor of claim 4 wherein the first oligonucleotide probe is linked through a 3' end to the substrate and the second oligonucleotide probe is linked through a 5' end to the substrate.

6. The sensor of claim 4 wherein the first oligonucleotide probe is linked through a 3' end to the substrate and the second oligonucleotide probe is linked through a 3' end to the substrate.

7. The sensor of claim 4 wherein the first oligonucleotide probe is linked through a 5' end to the substrate and the second oligonucleotide probe is linked through a 5' end to the substrate.

8. The sensor of claim 3 wherein:
   a first oligonucleotide probe with a first sequence, a second oligonucleotide probe with a second sequence, a third oligonucleotide probe with a third sequence, and a fourth oligonucleotide probe with a fourth sequence are covalently bound to the substrate, the first sequence and second subsequence complementary to a first subsequence and a second subsequence of a first strand of the target, respectively, and the third sequence and fourth sequence complementary to a third subsequence and fourth subsequence of a second strand of the target.

9. The sensor of claim 3 wherein:
   a first oligonucleotide probe with a first oligonucleotide-probe subsequence and a second oligonucleotide-probe subsequence are covalently bound to the substrate, the first oligonucleotide-probe subsequence complementary to a first target subsequence of the target and the second oligonucleotide-probe subsequence complementary to a second target subsequence of the target.

10. The sensor of claim 3 wherein:
    a first oligonucleotide probe with a first oligonucleotide-probe subsequence and a second oligonucleotide-probe subsequence is covalently bound to the substrate, the first oligonucleotide-probe subsequence complementary to a first target subsequence of a first strand of the target and the second oligonucleotide-probe subsequence complementary to a second target subsequence of the first strand target; and
    a second oligonucleotide probe with a third oligonucleotide-probe subsequence and a fourth oligonucleotide-probe subsequence is covalently bound to the substrate, the third oligonucleotide-probe subsequence complementary to a first target subsequence of a second strand of the target and the fourth oligonucleotide-probe subsequence complementary to a second target subsequence of the second strand target.

11. A method for preparing a sensor, the method comprising:
providing a sensor with a substrate and a signal-generation component coupled to the substrate that produces a sensor signal; and
associating two or more types of probes with, or binding two or more types of probes to, the substrate, each type of probe binding to a different binding site of a target, so that, when the sensor is exposed to the target, the target is bound to two or more probes at two or more binding sites to produce a change, in one or more physical characteristics of the substrate, probes, and/or other substrate-associated entities, that is detected by the signal-generation component, which generates a corresponding sensor signal.

12. The method of claim 11
wherein the substrate is the surface of an electrode;
wherein the one or more physical characteristics are modeled as a capacitance associated with the substrate, probes, and/or other substrate-associated entities; and
wherein the signal-generation component detects a change in impedance of a sensor circuit that includes the electrode as a circuit component.

13. The method of claim 11
wherein the probes are oligonucleotides bound to the substrate; and
wherein the target is a nucleotide polymer with multiple subsequences, each subsequence complementary to a different oligonucleotide probe.

14. The method of claim 13 further including:
covalently binding a first oligonucleotide probe with a first sequence and a second oligonucleotide probe with a second sequence to the substrate, the first sequence complementary to a first subsequence of the target and the second sequence complementary to a second subsequence of the target.

15. The method of claim 14 further including linking the first oligonucleotide probe through a 3' end to the substrate and linking the second oligonucleotide probe through a 5' end to the substrate.

16. The method of claim 14 further including linking the first oligonucleotide probe a 3' end to the substrate and linking the second oligonucleotide probe through a 3' end to the substrate.

17. The method of claim 14 further including linking the first oligonucleotide probe through a 5' end to the substrate and linking the second oligonucleotide probe through a 5' end to the substrate.

18. The method of claim 14 further including:
covalently binding a first oligonucleotide probe with a first sequence, a second oligonucleotide probe with a second sequence, a third oligonucleotide probe with a third sequence, and a fourth oligonucleotide probe with a fourth sequence to the substrate, the first sequence and second subsequence complementary to a first subsequence and a second subsequence of a first strand of the target, respectively, and the third sequence and fourth sequence complementary to a third subsequence and fourth subsequence of a second strand of the target.

19. The method of claim 13 further including:
covalently binding a first oligonucleotide probe with a first oligonucleotide-probe subsequence and a second oligonucleotide-probe subsequence to the substrate, the first oligonucleotide-probe subsequence complementary to a first target subsequence of the target and the second oligonucleotide-probe subsequence complementary to a second target subsequence of the target.

20. The method of claim 13 further including:
covalently binding a first oligonucleotide probe with a first oligonucleotide probe subsequence and a second oligonucleotide probe subsequence to the substrate, the first oligonucleotide probe subsequence complementary to a first target subsequence of a first strand of the target and the second oligonucleotide probe subsequence complementary to a second target subsequence of the first strand target; and
covalently binding a second oligonucleotide probe with a third oligonucleotide probe subsequence and a fourth oligonucleotide probe subsequence to the substrate, the third oligonucleotide probe subsequence complementary to a first target subsequence of a second strand of the target and the fourth oligonucleotide probe subsequence complementary to a second target subsequence of the second strand target.

* * * * *